United States Patent [19]

Leinders

[11] Patent Number: 4,595,009
[45] Date of Patent: Jun. 17, 1986

[54] PROTECTION CIRCUIT FOR IMPLANTABLE CARDIOVERTER

[75] Inventor: Robert Leinders, Sittard, Netherlands

[73] Assignee: Medtronic, Inc., Minneapolis, Minn.

[21] Appl. No.: 781,567

[22] Filed: Sep. 30, 1985

Related U.S. Application Data

[63] Continuation of Ser. No. 577,631, Feb. 6, 1984, abandoned.

[51] Int. Cl.[4] ............................................. A61N 1/36
[52] U.S. Cl. ................................................ 128/419 D
[58] Field of Search ............ 128/419 D, 419 PG, 908

[56] References Cited

U.S. PATENT DOCUMENTS

| | | | |
|---|---|---|---|
| 3,614,954 | 10/1971 | Mirowski et al. | 128/419 D |
| 4,210,149 | 7/1980 | Heilman et al. | 128/419 D |
| 4,300,566 | 11/1981 | Stindt et al. | 128/419 PG |
| 4,384,585 | 5/1983 | Zipes | 128/419 D |
| 4,440,172 | 4/1984 | Langer | 128/419 D |
| 4,475,551 | 10/1984 | Langer et al. | 128/419 D |

OTHER PUBLICATIONS

Winkle et al. "The Automatic Implantable Defibrillator: Local Ventricular Bipolar Sensing to Detect Ventricular Tachycardia and Fibrillation," *Am. J. Card.*, vol. 52, Aug. 1983, pp. 265–270.

Primary Examiner—William E. Kamm
Assistant Examiner—Mitchell J. Shein
Attorney, Agent, or Firm—Joseph F. Breimayer; Robert C. Beck; John L. Rooney

[57] ABSTRACT

An implantable medical device to deliver cardioverting energy to cardiac tissue in synchrony with detected ventricular depolarizations having a low power sensing and control circuitry and high power cardioversion circuitry, sharing a common lead and interface circuitry. The lead possesses a superior vena cava electrode and ring and tip electrodes intended to be placed in the ventricle. A sense amplifier is connected across the ring and tip electrode, and the cardioversion energy is delivered across the superior vena cava electrode and the ventricular electrodes. A circuit for protecting the low voltage sense amplifier circuits from high voltage cardioversion output pulses includes a triac which is electrically shorted across the ring and tip electrodes and the input terminals of the sense amplifier during the delivery of the stimulating pulse.

7 Claims, 6 Drawing Figures

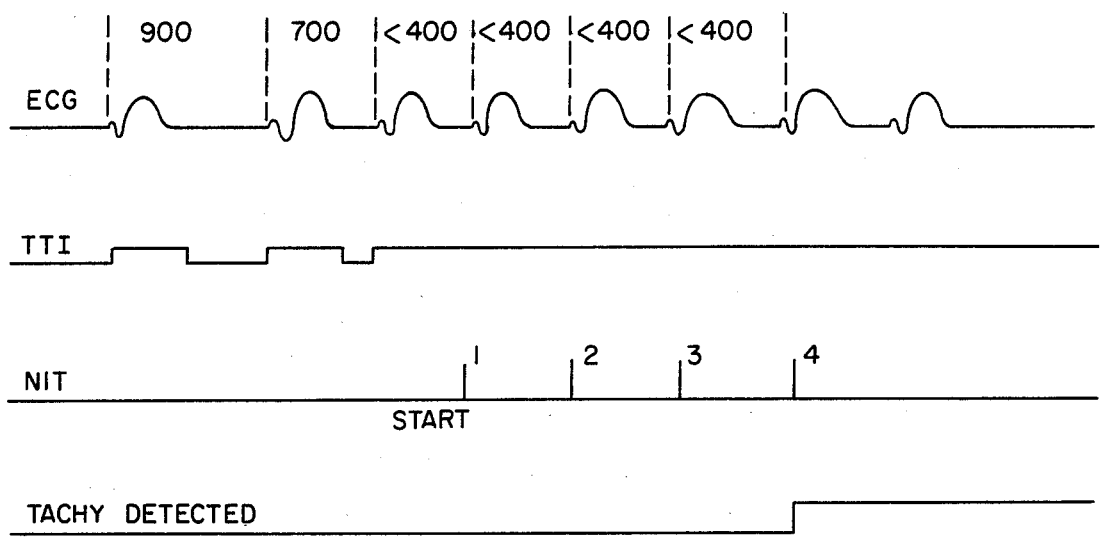
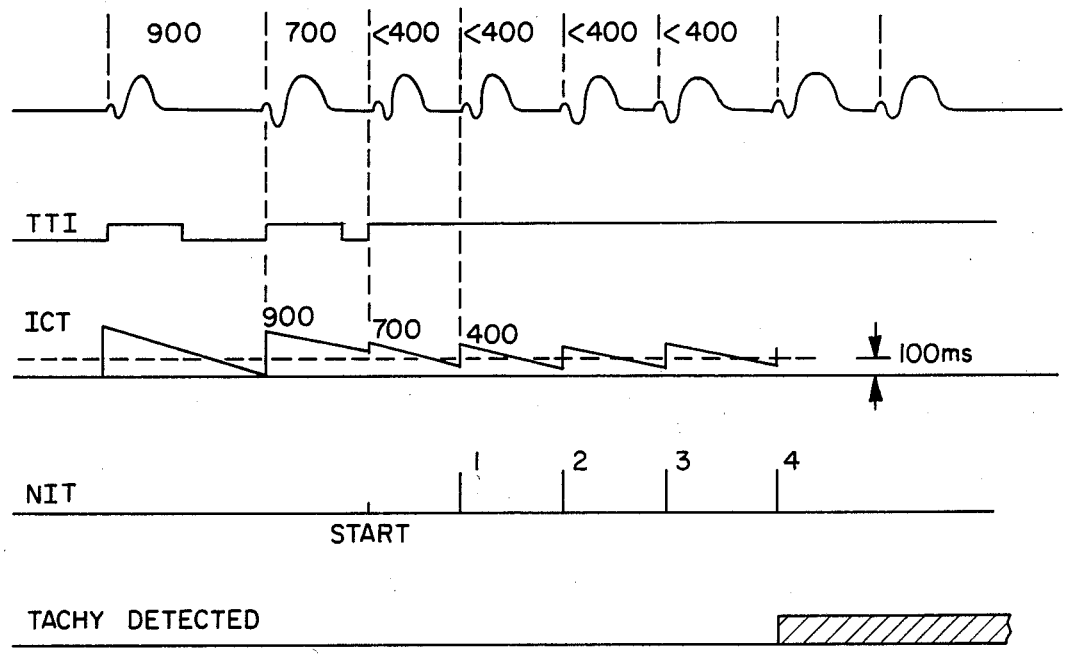

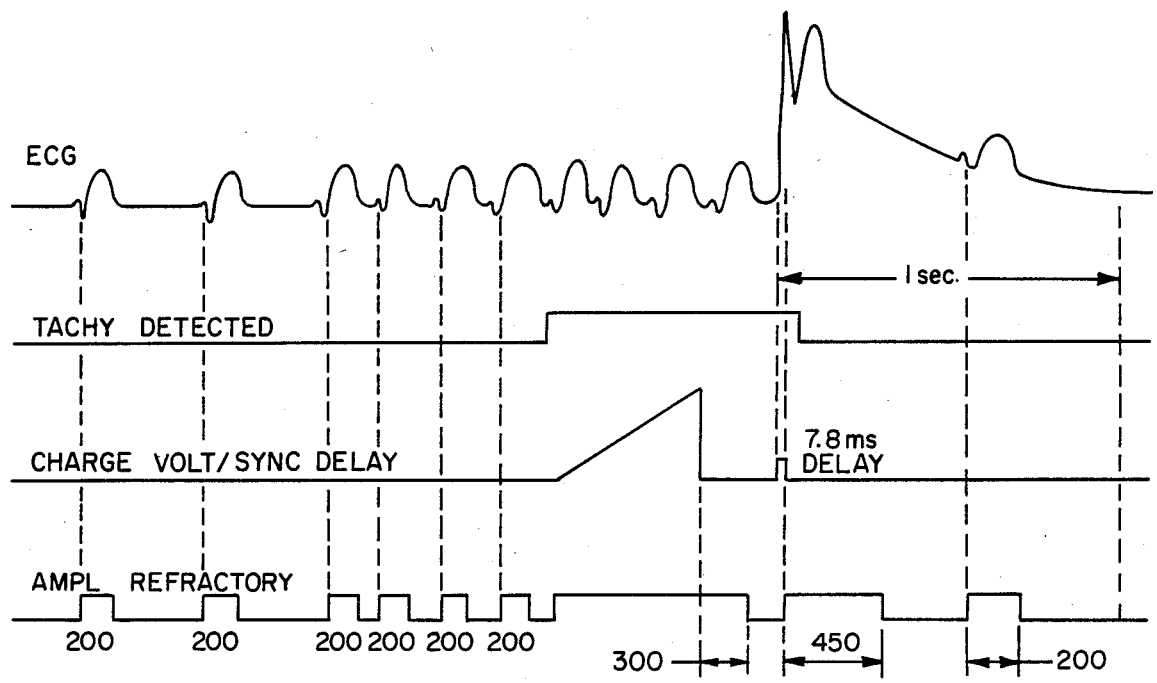

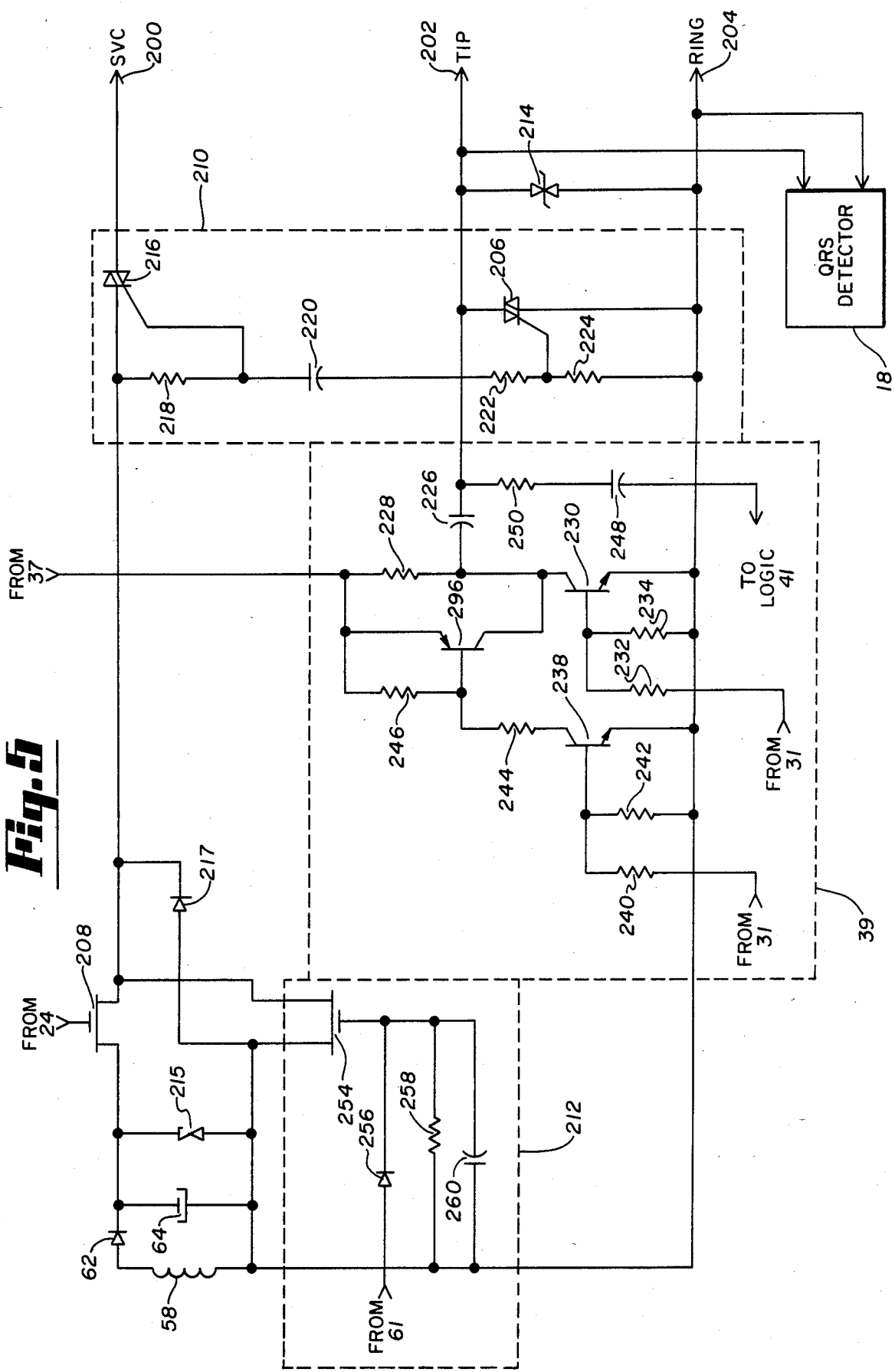

PROTECTION CIRCUIT FOR IMPLANTABLE CARDIOVERTER

This is a continuation of co-pending application Ser. No. 577,631 filed on Feb. 6, 1984, now abandoned.

BACKGROUND OF THE INVENTION

1. Field of the Invention

This invention relates to an implantable medical device that delivers sufficient electrical energy to cardiac tissue to terminate (cardiovert) tachycardias and thus restore normal sinus rhythm. An improved protection circuit prevents high voltage cardioversion pulses from damaging the sensing circuit of the device.

2. Description of the Prior Art

Implantable medical devices for the therapeutic stimulation of the heart are well known in the art from U.S. Pat. No. 3,478,746 issued to Wilson Greatbatch, which discloses a demand pacemaker. The demand pacemaker delivers electrical energy (5-25 microjoules) to the heart to initiate the depolarization of cardiac tissue. This stimulating regime is used to treat heart block by providing electrical stimulation in the absence of naturally occurring spontaneous cardiac depolarizations.

Another form of implantable medical device for the therapeutic stimulation of the heart is the automatic implantable defibrillator (AID) described in U.S. Pat. Nos. Re. 27,652 and Re. 27,757 to Mirowski, et al and the later U.S. Pat. No. 4,030,509 to Heilman et al. These AID devices deliver energy (40 joules) to the heart to interrupt ventricular fibrillation of the heart. In operation, the AID device detects the ventricular fibrillation and delivers a nonsynchronous high-voltage pulse to the heart through widely spaced electrodes located outside of the heart, thus mimicking transthoracic defibrillation. The Heilman et al technique requires both a limited thoracotomy to implant an electrode near the apical tip of the heart and a pervenous electrode system located in the superior vena cava of the heart. In practice, these devices have received limited usage due to the complexity of their implantation, their relatively large size and short operating life, and to the small numbers of patients who might benefit from it.

Another example of a prior art implantable cardioverter includes the device taught by U.S. patent application Ser. No. 58,847 to Engle, et al. This device detects the onset of tachyarrhythmia and includes means to monitor or detect the progression of the tachyarrhythmia so that progressively greater energy levels may be applied to the heart to interrupt the arrhythmia.

A further example is that of an external synchronized cardioverter, described in *Clinical Application of Cardioversion* in Cardiovascular Clinics, 1970,2, pp. 239-260 by Douglas P. Zipes. This external device is described in synchronism with ventricular depolarization to ensure that the cardioverting energy is not delivered during the vulnerable T-wave portion of the cardiac cycle.

Still another example of a prior art implantable cardioverter includes the device disclosed in U.S. Pat. No. 4,384,585 to Douglas P. Zipes. This device includes sensing circuitry to detect the intrinsic depolarizations of cardiac tissue and includes pulse generator circuitry to deliver moderate energy level stimuli (in the range of 0.1-10 joule) to the heart in synchrony with the detected cardiac activity.

The functional objective of this stimulating regime is to depolarize areas of the myocardium involved in the genesis and maintenance of re-entrant or automatic tachyarrhythmias at lower energy levels and with greater safety than is possible with nonsynchronous cardioversion. Nonsynchronous cardioversion always incurs the risk of precipitating ventricular fibrillation and sudden death. Synchronous cardioversion delivers the shock at a time when the bulk of cardiac tissue is already depolarized and is in a refractory state.

It is expected that the safety inherent in the use of lower energy levels, the reduced trauma to the myocardium, and the smaller size of the implanted device will expand the indications for use for this device beyond the patient base of prior art automatic implantable defibrillators. Since many episodes of ventricular fibrillation are preceded by ventricular (and in some cases, supraventricular) tachycardias, prompt termination of the tachycardia may prevent ventricular fibrillation.

Typically, the electrical energy to power an implantable cardiac pacemaker is supplied by a low voltage, low current, long-lived power source, such as a lithium iodine pacemaker battery of the types manufactured by Wilson Greatbatch Ltd. and Medtronic, Inc. While the energy density of these power sources is relatively high, they are not designed to be rapidly discharged at high current drains, as would be necessary to directly cardiovert the heart with cardioversion energies in the range of 0.1-10 joules. Higher energy density battery systems are known which can be more rapidly discharged, such as lithium thionyl chloride power sources. However, none of the available implantable, hermetically sealed power sources have the capacity to directly provide the cardioversion energy necessary to deliver an impulse of the aforesaid magnitude to the heart following the onset of tachyarrhythmia.

Generally speaking, it is necessary to employ a DC-DC converter to convert electrical energy from a low voltage, low current power supply to a high voltage energy level stored in a high energy storage capacitor. A typical form of DC-DC converter is commonly referred to as a flyback converter which employs a transformer having a primary winding in series with the primary power supply and a secondary winding in series with the high energy capacitor. An interrupting circuit or switch is placed in series with the primary coil and battery. Charging of the high energy capacitor is accomplished by inducing a voltage in the primary winding of the transformer creating a magnetic field in the secondary winding. When the current in the primary winding is interrupted, the collapsing field develops a current in the secondary winding which is applied to the high energy capacitor to charge it. The repeated interruption of the supply current charges the high energy capacitor to a desired level over time.

The delivery of the high energy cardioversion pulse is controlled by a memory and logic circuit which responds to a sensed tachycardiac according to programmable detection criteria. The pulse is delivered through an interface circuit which couples the pacing and cardioversion lead electrodes to the sensing circuit, the pacemaker output circuit and the high energy capacitor. The delivery of the high energy pulse creates a load on the sense amplifier due both to the energy of the pulse and the polarization after potentials that develop as the lead-tissue interface repolarizes following discharge.

The lead that is desirably employed in this system is described in U.S. Pat. No. 4,355,646. That lead has a large surface area anode electrode locatable in the superior vena cava and consisting of several ring electrodes electrically connected together. A ring and tip electrode are positioned at the distal portion of the lead adapted to be placed in the apex of the right ventricle. During cardioversion, the ring and tip electrodes are to be electrically connected together to form a large surface area cathode electrode. At other times the ring and tip electrodes are coupled to a sense amplifier or sensing circuit or pacing circuit. The present invention involves an improved circuit for effecting the electrical connection to avoid circuit damage and the elimination of polarization after potentials which interfere with sensing after cardioversion.

SUMMARY OF THE INVENTION

The implantable synchronous intracardiac cardioverter of the present invention employs sensing means responsive to cardiac depolarizations for producing a sense signal indicative of naturally occurring cardiac activity, such as ventricular R-waves; detection means responsive to the sensing means for detecting cardiac tachyarrhythmias, such a ventricular tachyarrhythmia, for producing a trigger signal; pulse generator means responsive to the detection of a tachyarrhythmia for delivering a cardioverting pulse to cardiac tissue in response thereto; voltage conversion means for providing a high energy power supply to said pulse generator means; and output circuit means for protecting the sensing means from damage done by the cardioverting pulse.

Additional circuitry may be included to provide a demand-pacing function in addition to the previous described cardioverting output. It is also anticipated that the amount of energy delivered can be controlled (programmed) by an external unit to reduce the joules delivered or increase the amount to a value that will be capable of terminating ventricular fibrillation. Finally, the device may be programmed to deliver the energy automatically after sensing particular parameters of a tachycardia or it can be programmed to deliver the energy only when an external magnet is held in place over the pulse generator.

BRIEF DESCRIPTION OF THE DRAWINGS

Other features and advantages of the present invention will become apparent from the following description of the invention and the drawings wherein:

FIGS. 2A and 2B are alternative timing diagrams illustrating the tachycardia detection criteria;

FIG. 3 is a timing diagram of the delivery of a high energy cardioversion pulse to the heart;

FIG. 5 is a circuit diagram of the improved output circuit.

DETAILED DESCRIPTION OF THE PREFERRED EMBODIMENT

As described hereinbefore, implantable cardioverters designed to treat ventricular tachyarrhythmias are generally known as described in the aforementioned U.S. Pat. No. 4,384,585. The present invention is embodied in a form of an implantable cardioversion system including a pulse generator and a lead, preferably a transvenous lead. The pulse generator preferably includes the components necessary to accomplish at least ventricular demand pacing at ordinary pacing energies and rates and circuitry for providing the cardioversion function. The lead preferably includes ring and tip electrodes located near one another in the distal portion of the lead adapted to be placed in the apex of the right ventricle and large surface area ring electrodes located more proximally along the lead body to be positioned in or near the superior vena cava as previously described. Very generally speaking, sensing and demand pacing is accomplished through the ventricular ring and tip electrodes, and cardioversion is accomplished between the ring and tip electrodes as a single indifferent or cathode electrode, and the superior vena cava electrode acting as the anode electrode.

The sense amplifier is connected between the ring and tip electrodes and, with appropriate logic, is capable of detecting normal R-waves to inhibit the operation of the pacing pulse generator and with appropriate detection logic, is capable of detecting abnormally high rate R-waves and operating the high energy cardioverter.

Figure 1:
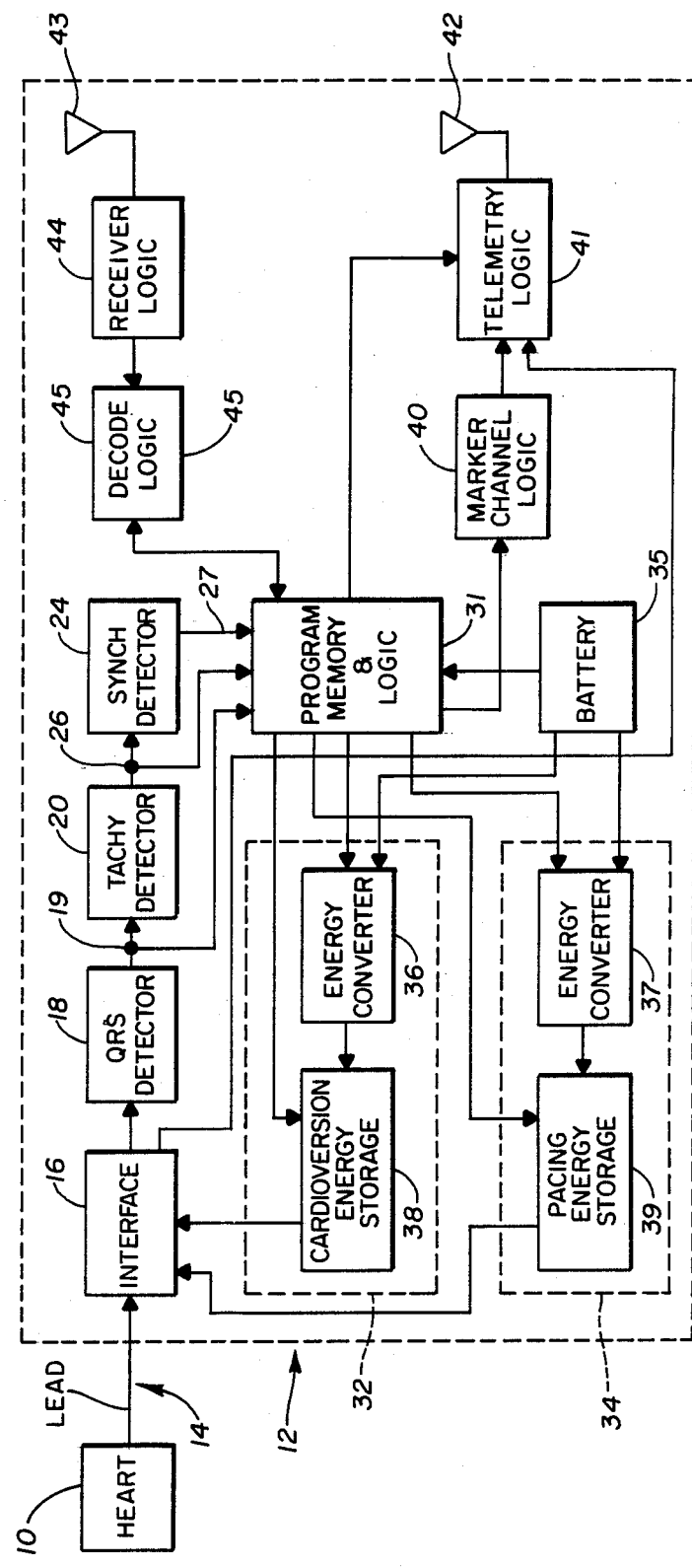
FIG. 1 is a block diagram showing the functional organization of the synchronous intracardiac cardioverter.

Referring now to FIG. 1, there is shown a block diagram similar to FIG. 2 of U.S. Pat. No. 4,384,585 in which the present invention may be practiced. In FIG. 1, the patient's heart 10 is coupled to the synchronous intracardiac cardioverter 12 through an appropriate lead 14 of the type described above and lead interface 16. The lead interface 16 includes circuitry to isolate the QRS detector 18 from the high voltage present during the delivery of a cardioverting pulse. Very generally the ring and tip electrodes are coupled together, in accordance with the present invention, by lead interface 16 during delivery of a cardioverting pulse.

Depolarization signals from the heart are communicated to the sensing amplifier or QRS detector 18 where they are detected. Such sense amplifiers are known in the art from U.S. Pat. No. 4,379,459 which is incorporated herein by reference. A subseqeunt tachyarrhythmia detector section 20 is coupled to the QRS detector through connection 19 to detect tachyarrhythmia based upon the electrogram information producing a tachy detect signal.

The synchrony detector 24 receives the tachy detect signal through connection 26. The output 27 of the synchrony detector is communicated to an appropriate logic section 31 which controls the cardioversion pulse generator circuitry 32 and triggers the delivery of the cardioverting pulse in response to the detected tachyarrhythmia. The synchrony detector 24 insures that the cardioverting pulse is delivered to the cardiac tissue concurrent with a detected ventricular depolarization of cardiac tissue. Circuit 32 includes a high energy converter 36 which converts low battery voltage into current and charges a capacitor in the high energy cardioversion energy storage circuit 38.

In operation, the electrogram information from the heart 10 is processed by the device which detects depolarizations of cardiac tissue and produces a sense signal indicative of this fact. This sense amplifier output is processed by a tachyarrhythmia detector 20 to determine the presence or absence of a tachyarrhythmia in a manner described hereafter.

If a tachyarrhythmia is detected, the logic section 30 will initiate a discharge of the energy storage section 38 to produce a cardioverting output. The synchrony detector 24 will insure that the energy is delivered to the heart 10 concurrently with a detected ventricular depolarization. The synchrony detector 24 may comprise combinatorial logic to activate the cardioverting pulse generator circuit 32 only when a tachy detect signal has been produced by the tachyarrhythmia detection circuitry. After the delivery of the cardioverting energy, the device will monitor the heart activity to determine if the arrhythmia has been terminated. If the arrhythmia is continuing, then additional cardioverting pulses will be delivered to the heart. These may be of the same or greater energy.

The synchronous intracardiac cardioverter is shown combined with demand pacing energy pulse generator circuitry 34 coupled to the lead interface 16. This pulse generator comprises a low energy converter 37 for charging the pacing energy storage circuitry 39 from the battery 35. In operation, logic 31 receives the signal from the QRS detector 18 and resets an escape interval timing system. If no cardiac depolarization is detected within the escape interval, a pacing pulse will be delivered to the heart. The integrated demand pacer with the synchronous cardioverter permits the device to initiate a cardiac polarization if a previously delivered cardioverting pulse has prevented or slowed the re-establishment of a normal sinus rhythm.

The power source 35 preferably consists of two lithium thionyl chloride cells, connected in series which produce an open circuit voltage of 7.33 volts to supply the cardioversion power circuit 32 and the backup pacing circuit 34 and one lithium iodine cell to provide the power for the remaining sensing and control circuits.

In addition, the preferred embodiment would be programmable and possess telemetry as shown, for example, in U.S. Pat. Nos. 4,401,120 and 4,324,382, respectively, each incorporated herein by reference. Among the programmable characteristics would be the mode (VOO, VVI and VVI with cardioversion), pacing rate, sensitivity, pulse width, tachy trigger interval, number of intervals to trigger, detection of interval change threshold, cardioversion pulse energy, patient therapy record and inhibit function. The receiving antenna 43, receiver logic 44 and decode logic 45 operate to effect programming of memory registers within program memory and logic 31 in the manner described in U.S. Pat. No. 4,401,120.

Among the telemetry functions, digital data, such as the device model identification, programmed parameter settings, cardioverter battery status, programming confirmation, the electrogram from the bipolar/ventricular lead, the marker channel exhibiting the amplifier sense after refractory period, the amplifier sense within tachy trigger interval, the ventricular pace pulse and the cardioversion pulse would all be transmitted out on command. The marker channel telemetry would be similar to that shown in U.S. Pat. No. 4,374,382 and is depicted as including market channel logic 40, telemetry logic 41 and transmitting antenna 42. (In practice, the transmitting antenna 42 and receiving antenna 43 may be a single antenna.) The pacing components, with the telemetry and marker channel features, preferably employ circuits disclosed in the aforementioned prior Medtronic patents and used in the prior Medtronic Spectrax-SXT ventricular pulse generator. In addition, it is contemplated that the DDD pacing components described in U.S. Pat. No. 4,390,020 could be incorporated into the cardioversion system to effect atrial and/or ventrical multimode pacing and/or cardioversion.

The additional programmable features of the preferred embodiment of the present invention, that differ from the prior patents and device mentioned above, comprises the additional cardioversion operating mode and the additional tachyarrhythmia recognition and cardioversion pulse energy parameters. These modes and parameters are stored in program memory and logic circuit 31 and directed to the tachy detector 20, and the cardioversion circuit 32.

The cardioversion output circuit 32 can only be activated when a tachycardia has been detected. Tachycardia recognition can be based on a sudden increase in heart rate combined with high rate or on high rate alone. The first method is called "the acceleration plus interval mode", and the second is called "interval mode". The "tachy trigger interval" (TTI) is an interval programmed into the pulse generator which recognizes sensed intervals between consecutive R-waves as indicative of a tachycardia if the sense intervals are shorter than this programmed tachy trigger interval. The "number of intervals to trigger" (NIT) is defined as that number of consecutive intervals shorter than the tachy trigger interval which will initiate a cardioversion. The "interval change threshold" (ICT) is defined as the number of milliseconds by which an interval has to be shorter than its predecessor in order to activate the tachy trigger interval and number of intervals to trigger criteria for tachycardia recognition. In order to detect such changes, the pulse generator continuously measures the difference between the last and second to last interval. If the interval change threshold is programmed equal to zero, the tachycardia recognition depends on the tachy trigger interval and number of intervals to trigger alone. Each of these factors, the TTI, NIT and ICT are programmable and are stored in memory and logic circuit 31.

In the acceleration plus interval mode, tachycardia is recognized if the interval change exceeds the interval change threshold while the succeeding intervals are also shorter than the selected tachy trigger interval for the selected number of consecutive intervals to trigger. In interval mode, tachycardia is recognized if the detected intervals are shorter than the selected tachy trigger interval for the selected consecutive number of intervals to trigger.

Thus the tachy detector 20 comprises a logic circuit having counters for timing out the intervals between the successive R-waves and comparing them to the programmed tachy trigger interval, interval change threshold, and number of intervals to trigger according to the acceleration and interval mode or the interval mode alone.

FIG. 2A depicts the timing of a sequence of R-waves where the tachy trigger interval is selected to be 400 milliseconds, the number of consecutive intervals to trigger equals 4 and the interval change threshold is programmed to zero. Thus, very simply, if four consecutive R-waves are sensed, each having an R-R interval less than 400 milliseconds, the tachyarrhythmia detection criteria are satisfied and a tachy detected signal is applied through logic 31 to the energy converter 36.

FIG. 2B depicts the acceleration plus interval mode tachyarrhythmia detection operation wherein the interval change threshold is programmed to 100 milliseconds. Thus, if the sensed R-R interval decreases by more than 100 milliseconds and the subsequent four R-R intervals are less than 400 milliseconds, the tachy detection criteria are satisfied and a tachy detected signal is again applied by logic 31 to the energy converter 36.

Figure 4:
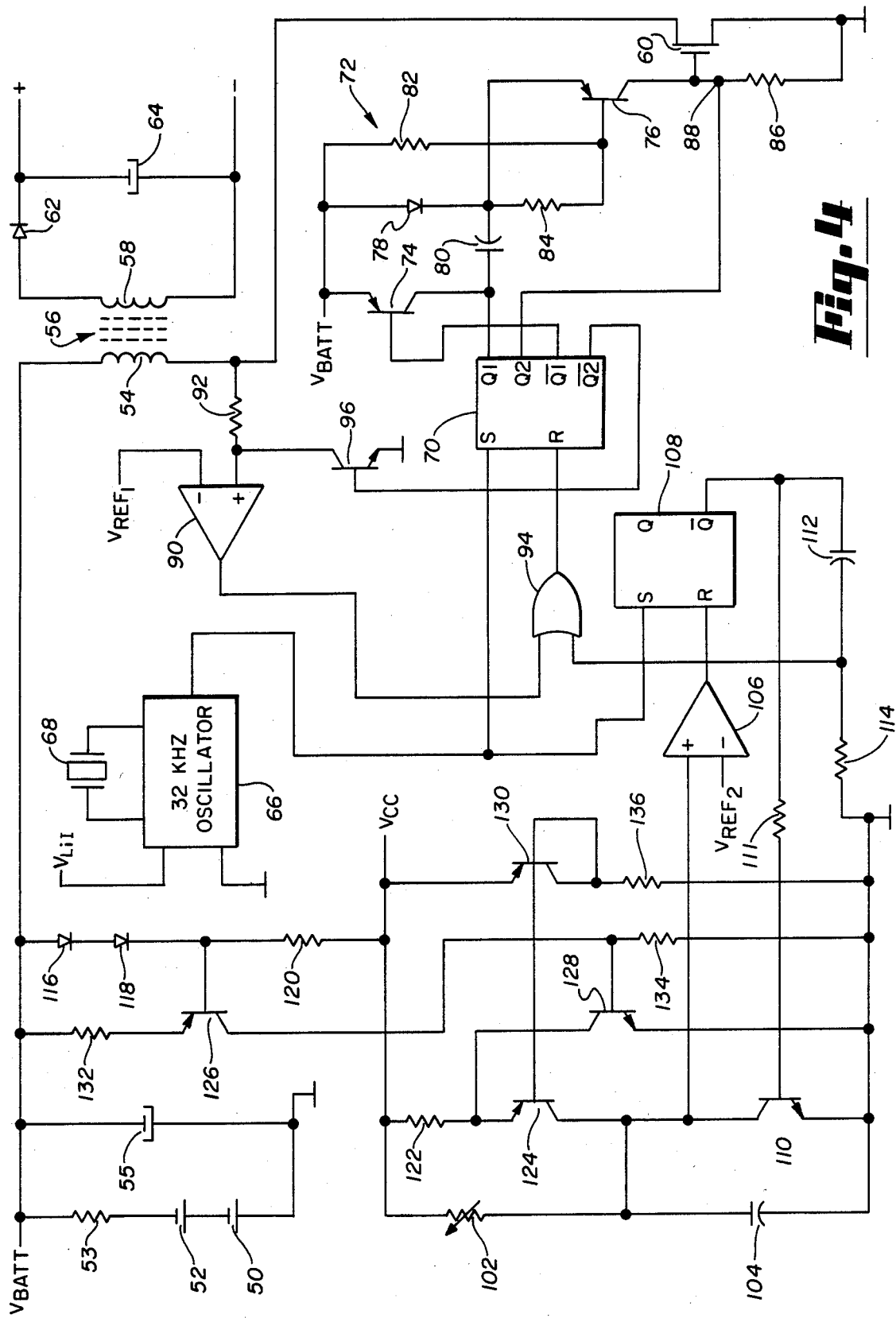
FIG. 4 is a circuit diagram of the DC-DC converter usable in the cardioverter.

When the selected tachycardia criteria has been fulfilled, the charging cycle for the cardioversion output stage 32 is initiated and controlled by the high energy charging circuit of FIG. 4.

FIG. 3 depicts a timing sequence of the detection and delivery of a cardioversion pulse in synchrony with a sensed R-wave. The refractory intervals and the cardioversion sense period are depicted as they occur following the delivery of a cardioversion impulse.

After charging to the programmed energy level, the cardioversion sense period is initiated during which a cardioversion pulse will be delivered in synchrony with a detected depolarization as described more specifically in U.S. Pat. No. 4,384,585. If sensing does not occur within the cardioversion sense period (1,000 milliseconds) following completion of capacitor charge period, the cardioversion pulse is aborted and the device reverts to VVI pacing. The VVI mode and tachycardia detection circuitry are also activated for 150 milliseconds after delivery of a cardioversion pulse. The amplifier refractory period will be 195 milliseconds in VVI mode and tachycardia detection, but 320 milliseconds after the charge period because of the switch on time. If an R-wave follows within the 320 milliseconds refractory period after charge completion, refractory is extended an additional 200 milliseconds. The cardioversion pulse is delivered 7.8 milliseconds delayed on the next sensed event still within the cardioversion sense period. If cardioversion remains unsuccessful after five attempts, the cardioversion will remain inactive until one of the tachy detection criteria is not met or a back up pacing pulse is delivered.

Referring our attention now to the charging circuit 34 of FIG. 4, the two series connected lithium thionyl chloride batteries 50 and 52 are shown connected to the primary coil 54 of transformer 56 and to the power FET transistor switch 60. The secondary coil 58 is connected through diode 62 to the cardioversion energy storage capacitor 64. Very generally, the flyback converter works as follows: When switch 60 is closed, current $I_p$ passing through the primary winding 54 increases linearly as a function of the formula $V = L_p dI/dt$. When FET 60 is opened, the flux in the core of the transformer 56 cannot change instantaneously so a complimentary current $I_s$ which is proportional to the number of windings of the primary and secondary coils 54 and 58 respectively starts to flow in the secondary winding 58 according to the formula $(N_p/N_S)I_p$. Simultaneously, voltage in the secondary winding is developed according to the function $V_s - L_s dI_s/dt$. The cardioversion energy storage capacitor 64 is charged thereby to the programmed voltage.

To simplify the drawings, optional connections have been omitted from FIG. 4 which would be included to connect the power source 50, 52 and the oscillator 66 to the circuit 32 upon command of the program memory and logic 31. Such switching circuits could be at the output of oscillator 66 and in the line between capacitor 55 and resistor 132 in FIG. 4. In addition, the circuitry for sensing the voltage on the capacitor 64, comparing it to the programmed value and disconnecting the power source means 50, 52 and oscillator 66 is not shown. In general, the voltage on capacitor 64 is reflected back through the transformer 56 and can be detected by comparison circuits coupled to the input winding 54 and the program memory and logic 31 to disconnect the power source 50, 52 and oscillator 66.

Each time the power FET 60 is switched into conduction, the current in the primary winding 54 starts to increase according to the preceding formula. At the moment that the power FET 60 is switched off, the field of the transformer 56 collapses and the secondary current starts to charge the capacitor 64. If the power FET 60 is switched on again before the secondary current has decreased to zero, the primary current starts to increase from a certain value (referred to as the pickup current) which is determined by the secondary current and the winding ratio. If this happens for several consecutive cycles, the primary current may go beyond the saturation current of the transformer 56. To avoid this, current through the power FET is monitored by sensing is drain voltage (the on resistance of power FET 60 is relatively constant) and power FET 60 is switched off when the current reaches a certain value. In order to suppress interference from this circuit, FET 60 is switched with a constant frequency and a variable duty cycle. The converter is driven at a frequency of 32 kz developed by oscillator 66, powered by the lithium iodine battery, which is driven by the crystal 68 and provides the basic timing clock for all the pulse generator timing and logic circuits. The power FET 60 is driven on and off by the the flip-flop 70 which is set at the leading edge of the clock pulses developed by the oscillator 66 and reset by an output signal from NR gate 94. Flip-flop 70 has a piar of output terminals $Q_1$, $Q_2$ which go high (ungrounded) when it is set and complementary outputs $\overline{Q}_1$, $\overline{Q}_2$ which go high when it is reset. The low state of the outputs $Q_1$, $Q_2$, $\overline{Q}_1$, $\overline{Q}_2$ may be at ground. Power FET 60 is driven into conduction each time flip-flop 70 is set through the operation of the voltage doubler circuit 72. The on time of power FET 60 is governed by the time interval between the setting and resetting of flip-flop 70 which in turn is governed either by the current $I_p$ flowing through the primary winding 54 or as a function of a time limit circuit, which contains further circuitry to vary the time limit with battery impedance (represented schematically by resistor 53).

The voltage doubler circuit 72 comprises a pair of driving transistors 74 and 76, a diode 78, a capacitor 80, and resistors 82, 84, 86. Assuming that flip-flop 70 is set and FET 60 is conducting, the resetting of flip-flop 70 causes the gate voltage of FET 60 to discharge through output $Q_2$. Capacitor 80 charges to battery voltage through diode 78 and output $Q_1$. When flip-flop 70 is again set, the battery voltage and the capacitor 80 voltage are additively applied to the emitter of transistor 76. Transistor 76 is biased to conduct by resistors 82 and 84, and when it switches on (when flip-flop 70 is set) $2V_{Batt}$ is applied to the gate of FET 60. FET 60 is switched on until the flip-flop 70 is again reset in the manner described hereinafter.

If primary current would be the only criteria for switching off power FET 60, then at low battery voltage (high internal impedance 53) the current would be so depleted that the saturation current level would not be reached before the next clock pulse. If that were to occur, power FET 60 would never be switched off and the flyback converter would cease functioning.

To avoid this problem, the on-time or duty cycle of power FET 60 is determined by an OR function of a time limit and a current limit. The current limit is determined by the first comparator 90 which compares the voltage drop across the source and drain of power FET 60 against a first voltage $V_{ref1}$. The signal is applied through resistor 92 to one input of the comparator 90, and whenever that signal exceeds reference $V_{ref1}$, the comparator 90 provides an output signal to one input of the OR gate 94. The signal applied to the OR gate 94 is passed through the reset input of flip-flop 70 which switches the $Q_1$ and $Q_2$ output low and switches the transistors 74 and 76 off in the manner previously described. During the time that the flip-flop 70 is reset, the $\overline{Q}_2$ output of flip-flop 70 is high and the transistor 96 is rendered conductive. Thus, when the FET 60 drain voltage equals $V_{ref1}$, comparator 90 resets flip-flop 70 via OR gate 94 switching power FET 60 off and the positive input of comparator 90 is grounded. When the flip-flop 70 is next set by a clock pulse, the power FET 60 is switched on and the positive input of comparator 90 is ungrounded.

Thus, by the means previously described, the duty cycle of the power FET 60 is current limited to efficiently operate the flyback converter as long as the batteries 50 and 52 provide a sufficiently high voltage and current. However, as current is drained from the batteries 50 and 52 to periodically recharge the high energy capacitor 64, the internal impedance 53 of the batteries will increase resulting in a lower available current. As the current lowers, the duty cycle of power FET 60 will tend to increase. The danger that the regulating circuitry 90-96 will be unable to reset the flip-flop 70 increases with time. The remaining circuitry of FIG. 4 provides a backup time limit circuit to the duty cycle while the batteries 50 and 52 exhibit normal voltage and current output and further compensating means for altering the time limit as the batteries 50 and 52 exhibit end-of-life voltage and impedance changes.

The time limit is determined by a one-shot circuit, comprising resistor 102, capacitor 104, comparator 106, flip-flop 108 and transistor 110. The time limit may be varied by altering the value of resistor 102 at the time of manufacture or through programming. The time limit interval is determined by the charge time of capacitor 104 through resistor 102 in comparison to a second reference voltage $V_{ref2}$. When voltage on capacitor 104 equals the reference voltage $V_{ref2}$, comparator 106 provides an output signal to the reset input of flip-flop 108 which provides a high output signal through coupling capacitor 112 to a second input of OR gate 94. Ordinarily it would be assumed that the time limit interval is longer than the current level interval detected by comparator 90. Therefore, the second input signal to the reset input of flip-flop 70 provided by the time limit interval circuit would have no effect. If, however, the current limit interval signal is delayed, then the time limit interval signal would provide the proper reset input signal to flip-flop 70.

When the flip-flop 108 is reset, its $\overline{Q}$ output goes high, and the transistor 110 is switched into conduction by the signal through resistor 111 to discharge capacitor 104 and ready the timing circuit for its next timing cycle which commences upon the delivery of the next clock impulse from oscillator 66 to the set input terminal of flip-flop 108. The time limit interval determining circuit therefore provides a backup system for insuring that the power FET 60 is turned off prior to the delivery of the next clock signal. The remaining circuit components are provided to modify the operation of the time limit interval circuit when the batteries 50 and 52 exhibit end-of-life behavior.

As batteries 50 and 52 deplete, the internal resistance 53 increases. Then as current is drawn from the batteries 50, 52 (when power FET 60 is rendered conductive), the voltage across the transformer 54 and power FET 60 may be reduced by the internal resistance related voltage drop of the batteries. Battery voltage also becomes too low to maintain $V_{cc}$ at its stabilized voltage and thus too low to ensure proper action of the control circuit. $V_{cc}$ voltage is a regulated voltage below battery voltage established by circuits not shown in FIG. 4 to power certain control and logic circuits.

As long as battery voltage is sufficiently above $V_{cc}$, collector current of transistor 126 is sufficient to generate enough voltage across resistor 134 to keep transistor 128 conducting. In turn, the emitter voltage of transistor 124 is pulled low by the conduction of transistor 128. Transistor 130 and resistor 136 tend to bias transistor 124 to conduct, but it is prevented from conducting by transistor 128. Capacitor 104 is only charged through resistor 102, and the time limit is established as described above.

When the voltage difference between battery voltage and $V_{cc}$ becomes lower, the collector current of transistor 126 decreases until the voltage generated across resistor 134 decreases and transistor 128 no longer conducts. Then the collector current of transistor 124 takes on a value, determined by resistor 122, which also charges capacitor 104 which is charged more quickly and decreases the time limit.

Thus, the compensation circuitry as described shortens the time limit interval whenever the battery voltage drops as a result of depletion and the consequent increase in internal resistance. The shortened interval reduces the mean current drain on the power source 50, 52 to prevent the battery voltage from collapsing further. The shortening of the time limit interval again provides assurance that the duty cycle of the on time of the power FET 60 is kept short enough to ensure that the flyback converter will work. This circuitry thus insures that the high energy capacitor 64 can be charged reliably and provide the energy necessary to provide the cardioversion function previously described whenever the batteries 50, 52 are able to deliver the required energy.

Turning now to FIG. 5, the interface or output circuit 16, the pacing energy storage circuit 39, the cardioversion energy storage circuit 38 and triggering and protection circuits 208, 210, 212, 215 and 217 of the cardioverter are shown in greater detail. The superior vena cava (SVC) electrode, the tip electrode and the ring electrode are adapted to be connected to terminals 200, 202 and 204, respectively, through the lead system 14. The ring and tip electrode terminals 202 and 204 are connected to the sense amplifier 18 and to the pacemaker output circuit 39, the triac 206 and to the marker channel logic 40. The high energy storage capacitor 64 is coupled through power FET 208 across the SVC terminal 200 and the series connected tip and ring terminals through the operation of the triac protection circuit 210. The further (optional) protection circuit 212 can be employed to provide a short circuit across the high energy capacitor 64 under certain conditions.

Protection of the pacing circuit and sense amplifier 18 from damage by external high energy interference, e.g. an external defibrillator, is accomplished by the standard back-to-back zener diode 214. Protection of the cardioversion circuit is effected by the breakdown voltage of triac 216 (+500 V) and, if this voltage is exceeded by the zener diode 215 and diode 217. Positive voltage will merely charge capacitor 64 via the reverse diode of FET 208 to the breakdown voltage of zener diode 215; negative voltage will be short circuited by diode 217.

In reference to the cardioversion operation, the capacitor 64 is charged during the charging cycle previously described. The synch detector 24 triggers the discharge of the capacitor by switching FET 208 conductive. The discharge is applied to the protection circuit 210.

Protection circuit 210 comprises the series connected triac 216 and the shunt triac 206, together with the biasing network 218, 220, 222 and 224. The initial discharge produces a voltage drop across the bias resistors which renders 216 and 206 conductive. In this fashion, the ring and tip electrodes are electrically connected in series just as the impulse is delivered. The R-C timing network of capacitor 220 and resistors 218, 222 and 224 insures that the triacs 206 and 216 are edge triggered by the voltage pulse. As current discharges from capacitor 64, the voltage decays until FET 208 switches off. Shortly thereafter, the current drops and triacs 206 and 216 switch off. In this way the protection circuit prevents an imbalance in after-potential or polarization from developing across the tip and ring terminals 202, 204 which are also the input terminals to the sense amplifier 18.

The pacing energy storage circuit 39 includes the pacing energy storage capacitor 226 and load resistor 228 which are connected to the $V_{cc}$ supply (developed by batteries 50, 52) from which capacitor 226 is charged. Capacitor 226 is discharged across the tip and ring terminals 202, 204 when transistor 230 is switched on in response to a pacing command delivered by the program memory and logic 31 through resistors 232 and 234.

During the charging cycle, a "fast recharge" of the type described in U.S. Pat. No, 4,406,286 is accomplished by command from the program memory and logic circuit 31. Very generally, for a short period following discharge of capacitor 226, transistor 236 is switched on to bypass load resistor 228 and accelerate the recharge time. Transistor 236 is switched on by the fast recharge signal applied to the base of transistor 238 through resistors 240, 242. Conduction of transistor 238 charges the bias potential at the junction of resistors 244, 246 and switches transistor 236 conductive.

The signal at tip electrode 202 is also applied by resistor 250 and capacitor 248 to the telemetry logic 41 for transmission through antenna 42 to receiving equipment outside the patient's body.

Although not shown in FIG. 5, it may be desirable to include a further resistor of about 50 K resistance across the tip and ring electrodes 202 and 204 to reduce polarization effects during pacing as taught in commonly assigned copending U.S. patent application Ser. No. 417,256 filed Sept. 13, 1982.

The additional protection circuit 212 comprises power FET 254, diode 256 and biasing resistor 258 and capacitor 260. This circuit operates to redundantly protect from misfires caused by a defect in power FET 208 or the synch detector 24.

Power FET 254 is kept conductive by a signal from gat terminal 88 of FET 60 (FIG. 4) applied through diode 256 to the gate of FET 254 until the capacitor 64 is charged up and FET 60 is no longer switched on and off. Each time FET 60 is switched on, current from circuit 72 also is applied to capacitor 260. Capacitor 260 switches FET 254 on after it charges to a certain voltage. Once circuit 72 stops supplying current (when capacitor 64 is charged up), current from capacitor 260 discharges through resistor 258, and FET 254 is rendered nonconductive. Thus, if power FET 208 were mistakenly fired prior to the complete charging of transistor 64, then the energy would be dissipated in power FET 254.

The invention described herein may advantageously be implemented in external cardioverters but is preferably employed in implantable cardioverters. The invention may also be implemented in any suitable analog or digital circuitry including software controlled custom or conventional microprocessors. These and other equivalent embodiments, modifications or uses of the invention will be apparent to those skilled in the art.

What is claimed is:

1. An implantable medical device for the electrical termination of an arrhythmic condition of the heart comprising:
   first terminal means adapted to be coupled to first electrode means positioned in relation to a first portion of the heart;
   second and third terminal means adapted to be coupled to second and third electrode means, respectively, positioned in relation to second and third portions, respectively, of the heart;
   power source means for providing electrical power to said device;
   means for detecting an arrhythmia of the heart and providing a trigger signal in response thereto, said detecting means coupled respectively to said second and third terminal means;
   cardioversion energy pulse generating means for providing a cardioversion energy pulse in response to a trigger signal; and
   protection circuit means responsive to the generation of a cardioversion energy pulse for electrically connecting said second and third terminal means together during delivery of a cardioversion energy pulse and for applying said cardioversion energy pulse between said first terminal means and said commonly connected second and third terminal means.

2. The device of claim 1 wherein said protection circuit means further comprises:
   first triggerable means electrically connected between said first terminal means and said cardioversion energy pulse generating means;
   second triggerable means electrically connected between said second and third terminal means;
   trigger circiut means electrically coupled to said cardioversion energy pulse generating means and to said first and second triggerable means for applying a trigger signal to said first and second triggering means; and
   cardioversion energy switching means responsive to said arrhythmia detection means for applying energy stored in said cardioversion energy pulse generating means to said trigger circuit means and to said first and second triggerable means whereby said trigger means trigger said first and second triggerable means into conduction.

3. The device of claim 1 wherein said protection circuit means further comprises:
   a first triac electrically connected between said first terminal means and said cardioversion energy pulse generating means;

a second triac electrically connected between said second and third terminal means;

impedance means electrically coupled to said cardioversion energy pulse generating means and to said first and second triacs for applying a trigger signal to the gates of said first and second triacs; and cardioversion energy switching means responsive to said arrhythmia detection means for applying energy stored in said cardioversion energy pulse generating means to said impedance means whereby said impedance means trigger said first and second triacs into conduction.

4. The device of claim 1 wherein said first electrode means are positioned outside the heart but adjacent to said first position.

5. An implantable medical device for delivering cardioverting energy to cardiac tissue to terminate an arrhythmic condition of the heart comprising:

first terminal means adapted to be coupled to electrode means introduced into the superior vena cava of the heart;

second and third terminal means adapted to be coupled to second and third electrode means, respectively, positioned in the ventricle of the heart;

power source means for providing electrical power to said device;

means for detecting an arrhythmia of the heart and providing a trigger signal in response thereto, said detecting means coupled respectively to said second and third terminal means;

cardioversion energy pulse generating means for providing a cardioversion energy pulse in response to a trigger signal; and protection circuit means responsive to the generation of a cardioversion energy pulse for electrically connecting said second and third terminal means together during delivery of a cardioversion energy pulse and for applying said cardioversion energy pulse to said first terminal means.

6. The device of claim 5 wherein said protection circuit means further comprises:

first triggerable means electrically connected between said first terminal means and said cardioversion energy pulse generating means;

second triggerable means electrically connected between said second and third output terminal means;

trigger circuit means electrically coupled to said cardioversion energy pulse generating means and to said first and second triggerable mans fro applying a trigger sginal to said first and second triggering means; and cardioversion energy switching means responsive to said arrhythmia detection means for applying energy stored in said cardioversion energy pules generating means to said trigger circuit means and to said first and second triggerable means, whereby said trigger circuit means trigger said first and second triggerable means into conduction.

7. The device of claim 5 wherein said protectin circuit means further comprises:

a first triac electrically connected between said first terminal means and said cardioversion energy pulse generating means;

a second triac electrically connected between said second and third output terminal means;

impedance means electrically coupled to said cardioversion energy pulse generating means and to said first and second triacs for applying a trigger signal to the gates of said first and second triacs; and cardioversion energy switching means responsive to said arrhythmia detection means for applying energy stored in said cardioversion energy pulse generating means to said impedance means, whereby said impedance means trigger said first and second triacs into conduction.

* * * * *